United States Patent [19]

Bellotti et al.

[11] Patent Number: 4,902,282
[45] Date of Patent: Feb. 20, 1990

[54] TUNED CYCLER SET

[75] Inventors: Marc Bellotti, Winnetka, Ill.; Ralph Davis, Burlington, Wis.; Arthur Lueders, Mundelein, Ill.

[73] Assignee: Baxter Travenol Labs. Inc., Deerfield, Ill.

[21] Appl. No.: 877,061

[22] Filed: Jun. 23, 1986

Related U.S. Application Data

[63] Continuation of Ser. No. 659,206, Oct. 9, 1984, abandoned.

[51] Int. Cl.⁴ .................. B01D 31/00; A61M 5/00
[52] U.S. Cl. ................................. 604/258; 604/118; 604/246; 604/256; 604/284
[58] Field of Search .................................. 604/4–6, 604/27–30, 34, 80, 81, 118–120, 123, 258, 283, 410; 137/606, 597

[56] References Cited

U.S. PATENT DOCUMENTS

| | | | |
|---|---|---|---|
| 3,520,298 | 7/1970 | Lange | 604/29 |
| 4,381,003 | 4/1983 | Buoncristiani | 604/29 |
| 4,525,156 | 6/1985 | Benusa et al. | 604/28 |
| 4,560,472 | 12/1985 | Granzow et al. | |
| 4,585,436 | 4/1986 | Davis et al. | |

FOREIGN PATENT DOCUMENTS 8402277  6/1984  World Int. Prop. O. ............ 604/29

Primary Examiner—C. Fred Rosenbaum
Attorney, Agent, or Firm—Charles R. Mattenson; Paul C. Flattery

[57] ABSTRACT

A flow set for administering peritoneal dialysis solution in automated peritoneal dialysis which comprises interconnecting flow conduits for connecting respectively with (1) a patient's catheter, (2) a container for warming dialysis solution, (3) a drain line, and (4) a source of dialysis solution. The flow conduit (4) for connecting with the source of dialysis solution defines at least three branching conduits having connectors on their respective ends for communication with separate containers of dialysis solution. In accordance with this invention, means are provided for causing the flow path resistance through the conduit (4) of the respective flow paths passing through each of said branch conduits to be substantially equal.

1 Claim, 1 Drawing Sheet

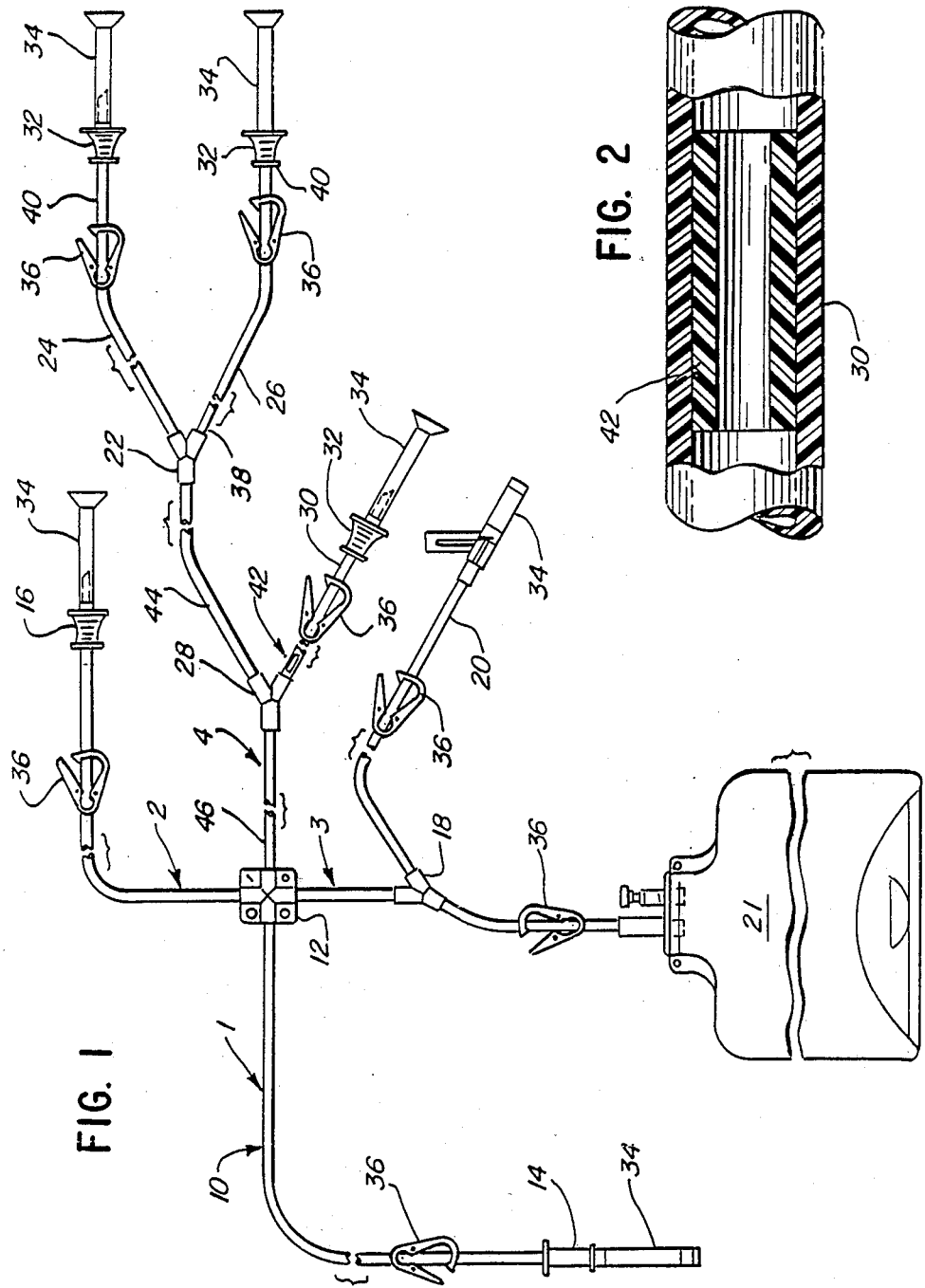

TUNED CYCLER SET

This is a continuation of application Ser. No. 659,206, filed Oct. 9, 1984 now abandoned.

BACKGROUND OF THE INVENTION

In Granzow et al. U.S. patent application No. 448,450, filed Dec. 10, 1982 automated peritoneal dialysis apparatus is disclosed in which interconnecting flow conduits communicate with (1) a patient's catheter, (2) a container for warming dialysis solution, (3) a drain line, and (4) a source of dialysis solution. The flow conduit (4) which communicates with the source of dialysis solution defines a plurality of branching conduits having connectors on their respective ends, for communication with separate containers of dialysis solution. An improvement on this device is disclosed in Davis et al. U.S. Pat. No. 4,585,436 filed Nov. 3, 1983.

The disposable flow sets that are used with automated peritoneal dialysis apparatus carry interconnecting flow conduits connecting respectively to the four locations listed above.

The source of dialysis solution is generally a plurality of dialysis solution bags so that the flow conduit (4) connecting with the source of dialysis solution typically defines at least three branching conduits having connectors on their respective ends for communication with separate connectors of dialysis solution. This is needed because automated peritoneal dialysis typically utilizes large quantities of peritoneal dialysis solution.

Typical automated peritoneal dialysis solution modalities are continuous cycling peritoneal dialysis (CCPD) and intermittent peritoneal dialysis (IPD). In both of these modalities, multiple cycles are performed by automated peritoneal dialysis apparatus, in which an aliquot of peritoneal dialysis solution is placed into the patient's peritoneal cavity, and, after a dwell period, is drained. Following this, added cycles automatically take place, in which another aliquot of peritoneal dialysis solution passes into the patient's peritoneal cavity, followed by drainage after the predetermined dwell period.

Accordingly, the patient can spend his sleeping hours or other time undergoing automated peritoneal dialysis in which three, four, or more complete peritoneal dialysis cycles can take place in an automatic manner.

Often, added medication such as insulin is desirably administered to the patient through the peritoneal dialysis solution. However, with previous designs of flow sets for automated peritoneal dialysis, it has frequently been necessary to add a uniform amount of medication to each container of peritoneal dialysis solution which is connected to the flow set, since the flow rates through the respective branches of the prior art sets that connect with the peritoneal dialysis solution containers are not uniform. If one adds medication to only one of the peritoneal dialysis solution containers, the concentration of medication passing into the peritoneal cavity of the patient in the various cycles of solution administration tends to vary widely. In some of the cycles, the concentration of medication in the solution administered would be very low. In other cycles of operation, the solution concentration could be very high, because the prior art set tends to draw solution in a nonuniform manner from the respective containers of dialysis solution. Hence, one is forced to divide up the dose of medicine and to administer it to multiple containers of peritoneal dialysis solution. This is very inconvenient, and also increases the risk that the medicine is administered incorrectly, for example, in non-aseptic manner, or in a wrong dose.

In accordance with this invention, a flow set for automated peritoneal dialysis is provided in which it becomes possible to add supplemental medication to only one of the several peritoneal dialysis containers in use. Because the flow characteristics of the respective branches that connect to the peritoneal dialysis solution containers are more equal than in the prior art, one can rely upon the set to automatically mix the medication-loaded solution from one container in a predictable and constant manner with the solution from other containers, so that the patient receives a relatively constant dose at all times, or varying but predetermined and predictable pattern of dosage if that is desired.

DESCRIPTION OF THE INVENTION

By this invention, a flow set for automated peritoneal dialysis is provided with comprises interconnecting flow conduits for connecting respectively with (1) a patient's catheter, (2) a container for warming dialysis solution, (3) a drain line, and (4) a source of dialysis solution.

The flow conduit for connecting with the source of dialysis solution defines at least three branching conduits having connectors on their respective ends for communication with separate containers of dialysis solution.

In accordance with this invention, means are provided for causing the flow resistance through conduit (4) of the respective flow paths passing through each of said branch conduits to be substantially equal. Thus, if two bags of dialysis solution at equal height are simultaneously opened to flow through the conduit (4) communicating with them, the simultaneous flow rates of solution out of said containers may be substantially equal. In the event that three containers are simultaneously flowing their contents through the flow set of this invention, for example, with the containers of dialysis solution being of equal elevation so that their pressure heads are equal, the flow from each of those containers may also be substantially equal.

It is preferred for the respective lengths of the flow paths through the flow conduit (4), connecting with the source of dialysis solution by way of two of said branching conduits, to be substantially equal. The third branching conduit may define a shorter flow path length than those of the first two branching conduits, with the third conduit including a flow-constricting bushing to equalize flow resistance.

The flow conduit (4) for connecting with the source of dialysis solution may define a first branching connection to which the first two branch conduits are connected. A second branching connection may be provided, spaced further from the outer end of the flow conduit (4) than the first branching connection. The third branching conduit may be connected to this second branching connection.

Flow conduits (1) through (4) may interconnect at a single location at their inner ends.

The flow variation between the respective branch conduits under essentially constant pressure conditions preferably varies by no more than essentially 12%, and most preferably no more than about 10%. Because of this, one may add medication to automated peritoneal dialysis equipment by injection into one of the peritoneal dialysis solution containers without great inconvenience, and without concern about intermittent overdosage and underdosage.

DESCRIPTION OF THE DRAWINGS

FIG. 1 is a plan view of a flow set for use with automated peritoneal dialysis apparatus.

FIG. 2 is a detailed, fragmentary view of the set of Figure 1, with portions broken away.

DESCRIPTION OF SPECIFIC EMBODIMENT

Referring to the drawing, a flow set 10 is disclosed, proportioned for disposable use in automated peritoneal dialysis apparatus. Particularly, the specific flow set shown is adapted for use with the automated Peritoneal Dialysis Cycler Machine sold by Travenol Laboratories of Deerfield, Illinois, or apparatus similar to those disclosed in the previously cited patents.

Four interconnecting flow conduits 1, 2, 3, and 4 are shown, intnerconnected at four-way X connector 12 at their inner ends for four-way interconnection. The specific design and other aspects of X connector 12 are as described in the prior Davis et al., U.S. Pat. No. 4,585,436, filed Nov. 3, 1983.

Flow conduit 1 communicates from X connector 12 to a connector 14 of conventional design, which is adapted to communicate with a catheter leading to the patient's peritoneal cavity.

Flow conduit 2 communicates with a conventional spike connection 16 which can communicate with a container of peritoneal dialysis solution. This container of solution may be placed at a heating and weigh station of the peritoneal dialysis apparatus, to warm the solution prior to admininstration to the patient.

Flow conduit 3 communicates through Y connector 18 with a drain line 20, and also a drain and weigh bag 21, which can be positioned at a weigh station of the peritoneal dialysis apparatus. Spent dialysis solution travels from the patient's peritoneal cavity to bag 21, where its volume may be determined by weighing. This volume may be electronically compared by the automated peritoneal dialysis apparatus with the original volume of fresh dialysis solution coming through flow conduit 2 from the heating bag into the peritoneum at the beginning of the dialysis cycle, as determined by a loss of weight of the heating bag as the solution is administered. From this, the ultrafiltration achieved through the dialysis cycle can be electronically calculated. Thereafter, bag 21 may be emptied by the action of a roller pump through drain line 20.

Flow conduit 4 defines a first branching connection 22 to which are connected a pair of branch conduits 24, 26. Second branching connection 28 is also provided to the flow conduit 4 at a position spaced further from the outer end of flow conduit 4 than first branching connection 22. A third branch conduit 30 is connected to second branch connection 28.

Each of branch conduits 24, 26, and 30 are terminated with conventional spike connectors 32, which connectors may be used to connect to bags or other containers of peritoneal dialysis solution. The solution bags are then mounted in their desired positions on the peritoneal dialysis apparatus. All connectors of set 10 may be initially closed with a protector member 34, as shown, and all flow lines may carry a flow occluding clamp 36, such as a Roberts clamp.

In accordance with this invention, means are provided for causing the flow resistance through conduit 4 of the respective flow paths passing through each of the branch conduits 24, 26, 30 to be substantially equal. This may be accomplished by adjustment of the relative lengths of the conduits 24, 26, 30 with respect to each other, and also by adjustment of the bore diameter and the like.

Specifically, the lengths of branch conduits 24, 26 are substantially identical. This specific length, measured from ends 38 of branch connector 22 to inner ends 40 of connectors 32 is 28 inches.

The length of branch conduit 30 may be less than the lengths of branch conduits 24, 26. Specifically, the length of branch conduit 30, measured from the outer end of branch connector 28 to the inner end of its associated connector 32 is 20 inches. For this reason, a tubular bushing 42 is positioned in the bore of flow conduit 4 to serve as a flow constricting means, to cause the flow resistance of conduit 30 to be substantially equal to the longer flow conduits 24, 26. This balance of flow resistance must not only include the flow resistance of the branch flow conduits 24, 26 outwardly from branch connector 22, but it must also include the flow resistance of length of conduit 44, where flow from branch conduits 24, 26 follows a common flow path.

Specifically, the tubing of flow set 10 may all have an inner diameter of 0.157 inch and an outer diameter of 0.235 inch. Bushing 42, which may be made of a piece of plastic tubing, may have an outer diameter of 0.180 inch being force fitted into the tubing of branch conduit 30 and also the tubing of Y connector 28, both of which may be made of a semiflexible polyvinylchloride material. The inner diameter of bushing 42 may be 0.130 inch, and the length of bushing 42 may be 1 inch. The length of tubing section 44 from Y connector 22 to Y connector 28 may be 7⅞ inches in length.

As the result of this, when set 10 is installed in automated peritoneal dialysis apparatus, and connectors 16, 32 are all connected to separate peritoneal dialysis solution bags, a roller pump may communicate with length of tubing 46 of flow conduit 4 to draw solution from the bags communicating with connectors 32 and to deliver it to the heater bag communicating with connector 16.

As previously described, it is frequently desirable to add supplemental medication to one of the bags communicating with connector 32, with the desire that the medication be predictably and uniformly mixed as solution is pumped through conduit length 46 in a relatively unvarying manner throughout the course of drainage of the bags in communication with connectors 32. Since the flow resistance through each of branch conduits 24, 26, and 30 is substantially equal, this desired condition will take place. As the result of this, the physician can add medication to any of the bags communicating with branch conduits 24, 26, or 30 with the confidence that a relatively uniform and predictable concentration of such medication will pass through conduit section 46 into the heater bag communicating with connector 16. The flow from each of conduits 24, 26, 30 will be substantially equal when open for flow and drawn by a roller pump operating on conduit portion 46.

The following specific example illustrates the advantage that can be obtained by equalizing the flow resistance of the branch conduits.

Two different flow sets made of polyvinylchloride to the design of FIG. 1 and substantially to the dimensions as specified above were tested, in comparison with a corresponding flow set which is commercially available. The commercially available set is very similar in appearance to FIG. 1, except that branch conduit 24 has a length from Y connector 22 to connector end 40 of 28 inches. Branch conduit 26 has a similar dimension of only 20 inches. The corresponding dimension for branch conduit 30 is 12 inches, and no bushing 42 is present.

The three flow sets were each mounted on a Travenol peritoneal automated cycler machine, Code 5C4400. Data was collected using the IPD mode. Bags of peritoneal dialysis solution were connected to connectors 16 and 32 and the machine operated in the normal manner of an IPD mode, with all clamps 36 being open so that flow access was available from all three branch conduits 24, 26, and 30.

A measured amount of creatinine was placed into the solution bag connected to branch conduit 24. A measured amount of urea was placed in the solution bag connected to branch conduit 26. A measured amount of inorganic phosphates was added tot he solution bag connected to branch conduit 30. One third of the measured amount of each of these materials was added to the heater bag connected to flow conduit 2.

As the machine proceeded through its IPD cycles, the respective concentrations of creatinine, urea, and inorganic phosphates found in the effluent coming through flow conduit 1 were analyzed. The selection of creatinine, urea, and inorganic phosphates as the indicator materials was governed by the fact that they are easily and quantitatively analyzable by automated electronic means.

Six so called dwell cycles, corresponding each to a peritoneal dialysis cycle, were performed. Six separate aliquots of dialysis solution were successively pumped by the action of a roller pump on length of tubing 46 to cause a mixture of the contents of the bags communicating with branch conduits 24, 26, and 30 to flow first through flow conduit 2 to the heated bag, and then back through flow conduit 2 and through flow conduit 1 to be collected for analysis.

The variations in concentrations of urea, creatinine, and inorganic phosphates in the effluent from conduit 1 throughout the six dwell cycles was noted. The standard deviation of these variations was determined, divided by the average amount of the portions of effluent in each cycle, and multiplied by 100, to obtain a coefficient of variation expressed as a percentage. Separate coefficients of variation were calculated for each of creatinine, urea, and inorganic phosphates. These coefficients of variation accordingly indicate the accuracy and uniformity of the individual flows through the branch conduits, and are as shown below:

Accrodingly, it can been seen that the sets made in accordance with this invention, while very similar in appearance to a corresponding set of the prior art, exhibit only a fraction of the flow variation from bags connected to their respective branch conduits. This provides the advantage described above, in which one may add medication to only one of the connected bags with confidence that the medication will be substantially uniformly distributed throughout the entire flow of peritoneal dialysis solution, because of the substantially equal flow resistance of the respective branch conduits. Specifically, the data above shows that with six cycles of delivering peritoneal dialysis solution through connector 14 of flow conduit 1, the flow through branch conduit 24 varies only by 2.2%, which is only about 37% of the flow variation of the prior art flow set.

The average flow variation of the two sets of this invention through branch conduit 26 is 6.8%. This is a substantial reduction from the 9.1% flow variation of branch conduit 26.

The average flow variation found in branch conduit 30 of the sets of this invention is 8.1%. This is only about 38% of the flow variation of the corresponding branch conduit of the prior art set described above.

The above has been offered for illustrative purposes only, and is not intended to limit the scope of the invention of this application, which is as described in the claims below.

That which is claimed:

1. An administration set for use in association with a peritoneal dialysis cycler machine having predetermined locations for supporting first, second, and third peritoneal dialysis solution containers, said administration set comprising:

first, second, third, and fourth branch conduits each having essentially the same interior diameter, said first and second branch conduits being essentially equal in length, said third branch conduit being longer than said fourth branch conduit, a first junction joining an end of said first branch conduit and an end of said second branch conduit in common flow communication with an end of said third branch conduit, the other ends of said first and second branch conduits being individually attachable in flow communication with, respectively, the first and second containers of peritoneal dialysis solution, a second junction joining the other end of said third branch conduit in flow communication with an end of said fourth branch conduit, the other end of said fourth branch conduit being attachable in flow communication with the third container of peritoneal dialysis solution, and means defining a bushing located within said fourth branch conduit for restricting fluid flow so that, when the first, second, and third containers are located at their predetermined locations on the cycler machine, the resistance to fluid flow between the third container and said second junction is automatically made essentially equal to the resistance to fluid flow between either the first or second container and said second junction.

* * * * *